United States Patent [19]

Gruelich et al.

[11] Patent Number: 6,087,101
[45] Date of Patent: Jul. 11, 2000

[54] OPTICAL CHARACTERIZATION OF NUCLEIC ACIDS AND OLIGONUCLEOTIDES

[76] Inventors: Karl Otto Gruelich, 25-27 Ploeck; Claus Seidel, 8 Brueckenstrasse, both of 6900 Heidelberg; Juergen Wolfrum, 2 Suedring, 3405 Rosdorf, all of Germany; Manfred Auer, 38/1 Lowatschekgasse, A-2340 Moedling, Austria; Matthias Gautel, 25 Mathystrasse, 7500 Karlsruhe 1, Germany; Roger Goody, 16 Dossenheimer Weg, 6802 Ladenburg, Germany; Siegfried Labeit, 17 Im Boden, 6919 Bammental, Germany

[21] Appl. No.: 08/990,734

[22] Filed: Dec. 15, 1997

Related U.S. Application Data

[63] Continuation of application No. 07/525,038, May 18, 1990, abandoned.

[51] Int. Cl.$^7$ ........................................................ C12Q 1/68
[52] U.S. Cl. ........................................................ 435/6
[58] Field of Search ........................... 435/6, 91.5; 436/94

[56] References Cited

U.S. PATENT DOCUMENTS 5,332,666  7/1994  Prober et al. ........................... 435/91.5

*Primary Examiner*—Lisa B. Arthur
*Attorney, Agent, or Firm*—Keil & Weinkauf

[57] ABSTRACT

A method for the enzymatic sequencing of DNA is disclosed which uses dideoxythio-nucleotides or dideoxyamino-nucleotides as terminators that are labeled with one or two fluorescent dyes coupled to the terminators either before or after polymerization. The dye labeled DNA fragments are separated in a single lane of a separation system and then the terminal bases of each of the fragments are identified by measuring the fluorescent lifetime of the dye attached to the terminators.

5 Claims, No Drawings

OPTICAL CHARACTERIZATION OF NUCLEIC ACIDS AND OLIGONUCLEOTIDES

CROSS-REFERENCE TO RELATED APPLICATIONS

This is a Continuation Application of application Ser. No. 07/525,038, filed on May 18, 1990, now abandoned.

The present invention relates to a method for the optical characterization of nucleic acids and oligonucleotides.

BACKGROUND OF THE INVENTION

Accurate analysis of nucleic acids (single- and double-stranded DNA or RNA) is of central importance for understanding life processes in cells and, in particular, for identifying the information contained in the DNA.

Methods have already been developed for analyzing nucleic acid sequences. The classical method for sequencing (Proc. Natl. Acad. Sci. USA 74 (1977) 5463) nucleic acids, especially DNA, is slow, susceptible to error and very difficult to automate. This is why there has been development recently of some methods which employ fluorescence labeling of DNA (J. Biochem. Biophys. Meth. 13 (1986) 315, Nature 321 (1986) 674, Science 238 (1987) 336). However, none of these methods makes use of specific interactions between dye and nucleic acid in order to characterize the DNA. Hence all the known methods require either several dyes or several lanes in the separation medium.

The use of thionucleotides for DNA sequencing by limited exonuclease digestion is described in WO 86/07612. However, this method is not very suitable for automation.

Furthermore, thionucleotides are employed in investigations of cells because of the limited digestability by exonucleases (Nucleic Acids Res. 18 (1990) 829). Reports of the use of aminonucleotides as terminators in DNA sequence analysis have mentioned only radioactive detection, with an indication of the possibility of coupling other detector molecules to the free amino group (Nucleic Acids Res. 12 (1984) 1671).

Moreover, several methods have been developed for visualizing DNA in in situ hybridization (Proc. Natl. Acad. Sci. USA 78 (1981) 6633, Exptl. Cell. Res. 153 (1984) 61, Histochem. 85 (1986) 1). However, these methods are very time-consuming or, owing to unavoidable deficiencies, give results which are unreliable in some cases.

DNA in which thionucleotides are incorporated can be detected in gels by coupling suitable fluorescent dyes (Biochem. 28 (1989) 261). However, the dye-labeled single-strand DNA is unstable under the conditions of electrophoresis and can therefore not be isolated pure as a fluorescent probe for the hybridization.

A method for the fluorescence labeling of nucleic acids by enzymatic transfer of a dye-labeled thionucleotide has also been described (Nucleic Acids Res. 12 (1984) 1791). However, a maximum of only one dye molecule per DNA strand can be coupled to the DNA by this method.

SUMMARY OF THE INVENTION

The present invention relates to a method for the characterization of nucleic acids and/or oligonucleotides which comprises coupling detector molecules to the nucleic acids and/or oligonucleotides, which reveal, on the basis of interactions, to which nucleotide the coupling has taken place.

Oligonucleotides are defined as those containing up to 20 nucleotides. Molecules composed of more than 20 nucleotides are called nucleic acids herein.

DETAILED DESCRIPTION OF THE INVENTION

Optical characterization of the nucleic acid or the oligonucleotide means that the bases of the nucleotides are, owing to the coupling on of a florescent dye, identified on the basis of optical properties, and the nucleic acid or the nucleotide is detected.

The only dyes suitable for characterization are those which display differences in quenching, i.e. have different interactions between the dye and the four possible terminal bases. A mechanism suitable for this is fluorescence quenching by photoinduced electron transfer (Chem. Rev. 86 (1986) 401). The quenching is determined by the HOMO (highest occupied molecular orbital) and the LUMO (lowest unoccupied molecular orbital) energies of the reactants. The orbital energies can be determined electrochemically. A suitable measure of these interactions is the fluorescence lifetime of the dye.

Suitable dyes are fluorescent dyes such as fluoresceins, rhodamines and oxazines.

Dyes particularly suitable for fluorescence quenching by light-induced electron transfer are: coumarins—preferably 7-amino-4-methylcoumarin, carbostyrils—preferably 7-amino-4-methylcarbostyril, and oxadiazoles—preferably 2-(4-biphenylyl)-5-phenyl-1,3,4-oxadiazole.

It is crucial for the suitability of a dye for the fluorescence quenching that its orbitals are able to interact with the HOMO and/or the LUMO of the DNA bases.

The present invention is particularly suitable for use for sequencing because, for the first time, the information contained in the specific chain breakages is utilized for the identification owing to the coupling of fluorescent dyes to the terminal nucleotides.

The present invention also relates to a method for labeling nucleic acids and oligonucleotides, which comprises incorporating thionucleotides into the nucleic acids and oligonucleotides and subsequently specifically coupling detector molecules covalently to the sulfur of the thionucleotide.

Labeling of the nucleic acid or of the oligonucleotide means that the nucleic acid or the oligonucleotide is made visible or detectable.

Detector molecules which can be used are, inter alia, dyes, radioactive labels, spin labels or antigens. The latter can be visualized in an antigen-antibody reaction with dye-labeled antibodies. Detection can be carried out in a conventional manner, eg. by fluorescence microscopy, spectroscopy or using the blot technique.

Thionucleotides suitable for incorporation into the nucleic acid or oligonucleotide are those which have an SH group in the 2' or 3' position of the pentose, eg. 2',3'-dideoxy-3'-thioribose, 2',3'-dideoxy-3-thioxylose, 2',3'-dideoxy-2'-thiorabinose, 2'-deoxy-2'-thioarabinose, 3'-deoxy-3'-thioxylose, 3'-deoxy-3'-thioribose. Particularly suitable thionucleotides are those in which the sulfur is attached to phosphorus, i.e. the deoxynucleotide 5'-thiophosphates and nucleotide 5'-thiophosphates.

The thionucleotide is incorporated at the terminus and/or at any desired points of the nucleic acid or the oligonucleotide by chemical or, preferably, enzymatic means. Incorporation at the terminus is used for sequence analysis, and incorporation at any desired points is for labeling the nucleic acids and oligonucleotides.

Aminonucleotides are suitable only for incorporation at the terminus by enzymatic means in DNA sequence analysis. Suitable aminonucleotides are those which have the amino group in the 2' or 3' position of the pentose, eg. 2',3'-dideoxy-3'-aminoribose, 2',3'-dideoxy-3'-aminoxylose, 2',3'-dideoxy-2'-aminoarabinose, 2'-deoxy-2'-aminoarabinose, 3'-deoxy-3'-aminoxylose and 3'-deoxy-3'-aminoribose.

Enzymatic incorporation of the amino- or thionucleotide at the terminus is carried out by template-controlled polymerization of nucleic acids with a polymerase in the presence of a modified terminator. Modified terminators are defined as dideoxynucleotide α-thiophosphates, or triphosphates of the abovementioned dideoxypentoses with an $NH_2$ or SH group.

Enzymatic incorporation of thionucleotides at any desired points in a DNA is preferably carried out by enzymatic nick translation in the presence of a DNAase and a DNA polymerase. An example of a suitable DNAase is deoxyribonuclease I from bovine pancreas. Examples of suitable DNA polymerases are polymerase I from *E. coli*, the Klenow fragment and T7 DNA polymerase.

Chemical incorporation of the thionucleotides is carried out in a conventional manner (cf. Winnacker: Gene und Klone, VCH Verlagsgesellschaft, D-6940 Weinheim, 1985, pages 44 et seq.). Thionucleotides are simply used in place of nucleotides.

The dye can be directly bonded to the hetero atom of the amino- or thionucleotide when the dye has a suitably activated group for coupling to the hetero atom. Examples of such groups for sulfur are α-haloacetyl, maleimido and bromoallyl groups. Suitable groups for coupling to nitrogen include the isothiocyanate and the N-succinimidyl group. Dyes of this type are described, for example, in the Bioprobes catalog from Molecular Probes, Eugene, USA.

The dye-labeling can also be carried out indirectly. This entails binding of a hapten activated as described above. This can take place by means of an antigen-antibody reaction with dye-labeled antibodies or by coupling of an enzyme, such as peroxidase, which elicits a color reaction (cf. Proc. Natl. Acad. Sci. USA 70 (1981) 2238, Exptl. Cell Res. 153 (1984) 61, Histochem. 85 (1986) 1).

It is also possible for the terminators with an SH or $NH_2$ group in the sugar residue to be dye-labeled separately before being used in the enzymatic polymerization because they are accepted as substrates of the enzyme.

The present invention makes it possible for the first time to utilize in an analytical detection the information contained in the specific modification of the properties of the coupled detector molecule. Such modifications have hitherto been regarded as undesirable and, for this reason, attempts have been made to avoid them by the way of carrying out the experiment.

The method according to the invention has the following additional advantages:
1. The dye-labeling of the DNA can take place immediately before the fractionation or the visualization. This means that virtually all the properties of the DNA are retained up to the visualization. There is no essential alteration in the nucleotides in the DNA by the replacement of an oxygen by a sulfur or of a hydrogen by an amino or SH group. In this respect the novel method differs distinctly from known methods.
2. The dye-labeling reaction takes place rapidly and quantitatively under mild conditions.

Application of the present invention to DNA sequencing makes it possible for the first time to use one lane for all bases and only one dye for identifying the bases. This 1-lane/1-dye strategy increases the accuracy of analysis and considerably simplifies DNA sequencing because it is possible to use all separation systems, especially including capillary electrophoresis and HPLC.

No wrong stops are observed with the method according to the invention, because they are not labeled. Wrong stops are chain breakages which take place non-specifically in the DNA and for which there is at present no explanation.

It is possible, by the choice of coupling the fluorescent dye to the thiophosphate residue of the terminator, to identify not only the last but also the penultimate DNA base by interactions. This doubling of information is a considerable advantage for the reliability of the evaluation.

The use of dideoxynucleotides additionally modified in the base enhances the accuracy of resolution of the optical characterization of the terminal nucleotides. The modification in the base comprises, for example, replacement of carbon by nitrogen or vice versa, eg. by use of 3,7-dideazapurine, 5-aza-7-deazapurine or 6-azacytosine.

The 1-lane/2-dye strategy has the same action as the 1-lane/1-dye strategy and, moreover, utilizes the spectral differentiation of the dyes in combination with the fluorescence lifetimes.

The novel method makes use for the first time of the measurement of the fluorescence lifetime of dyes coupled to DNA molecules. The measurement is very sensitive because it cannot be influenced by the stray light from the excitation, which otherwise interferes with steady-state measurements. The accuracy of measurement is thereby increased. In addition, the measurement of the fluorescence lifetime allows the bases to be identified, even when their bands overlap, because the duration of the lifetimes is not influenced by the overlap. The lifetime can be measured, for example, by single shot, single photon counting or with a streak camera, excitation being brought about by a fast flashlamp or a short laser pulse of suitable wavelength.

The sequencing method according to the invention is based essentially on the following prerequisites:
1. Template-controlled polymerization with a modified terminator so that each DNA strand has a specific coupling site at the end.
2. Coupling of a fluorescent dye with the property that the terminal nucleotides are identified by the differences in fluorescence lifetime.
3. Separation of the DNA fragments on one lane by capillary electrophoresis, HPLC or electrophoresis.

This method is also suitable for automation. Since great efforts are currently being made to speed up DNA sequencing, the replacement of the radioactive labeling by a fluoresent dye, the 1-lane strategy and the resultant facilitation of automation represent a considerable step in this direction.

Another area of use of specific dye coupling to DNA is represented by in situ hybridization. Besides the time saved by replacing radioactive labeling by fluorescent dyes, there is also interest in the simultaneous detection of several hybrids, which can be achieved by color reactions.

In the dye-labeling methods in the known sequencing methods, the dye has been directly bonded to the base of the nucleotide or to the first sugar residue of the primer. Modifications of this type by additional, usually aromatic, systems interfere too greatly with in situ hybridization so that, in the current methods, one is limited to chemical modification, by binding of haptens and by coupling sites, of the bases before the hybridization, in order to carry out the dye coupling after the hybridization. The chemical properties are greatly influenced by the drastic modifications.

The base modification also greatly influences the hybridization properties, as manifested by altered melting temperatures and altered enzyme affinities.

The invention has the following advantages with regard to the dye coupling:
1. For the first time it is not the base which is modified but the phosphate or sugar residue.
2. For the first time it is possible to dye-label all the bases or only a desired region.
3. It is possible to increase the dye density and thus improve the sensitivity.
4. All molecules required for the indirect dye-labeling can be coupled.

The in situ hybridization method according to the invention is essentially based on the following prerequisites:
1. The nucleic acid probes can be prepared by nick translation with thiodeoxynucleotides, by template-controlled polymerization or by chemical synthesis.
2. The nucleic acid probe with the required content of incorporated thionucleotides is employed for the in situ hybridization.
3. The coupling and dye-labeling are carried out only after the hybridization.

This method is at least 4× as sensitive as the above methods because all the bases and not just one base can be dye-labeled. It is possible to prevent mutual quenching of adjacent dyes by adding lipophilic solvents such as hexafluoroisopropanol. It is possible further to increase the dye density by using coupling reagents carrying several dyes. The same objective can also be achieved by coupling an antigen and detecting it by antigen/antibody reactions with fluorescence-labeled antibodies.

USE EXAMPLES

The dye used for the dye labeling in all the examples was 7-(2-ethylaminocarbonyliodomethyl)-4-methylcoumarin(=4,7-IEME-COUM).

1. Coupling of a Dye to a Thiomononucleotide 13 mg (0.034 mmol) of 4,7-IEME-coum were dissolved in 625 µl of dimethylformamide. Then 300 µl of 1 M tris/HCl buffer (pH 7.4) and 325 µl of 83 mM (0.027 mmol) of thio-AMP in aqueous solution were rapidly added. After 1 min at 5° C., the reaction was complete and thio-AMP was no longer detectable.

The reaction solution was fractionated by column chromatography on ®QAE-Sephadex A25 with triethylammonium bicarbonate, pH 7.5 (gradient elution: 20–150 mM; 2×2 l) at 4° C. The fluorescent fraction contained the product in approximately 100% yield.

The purity according to HPLC analysis was 80% (reversed phase $C_{18}$ silica gel with gradient elution: from 50 mM $KHPO_4$ buffer (pH 6.5) to acetonitrile/buffer (1:1) in 50 min). The product was eluted after about 20 min and contained no fluorescent impurities.

The dye can be coupled to thio-TMP, thio-GMP and thio-CMP and the corresponding thiodeoxynucleotides can be coupled in a corresponding manner.

2. Identification of a Thionucleotide by Means of Fluorescence Lifetimes τ.

The nucleotides coupled to the dye (D) are called AD, CD, TD and GD. Single shot measurement was chosen for measuring the lifetime.

| | | | |
|---|---|---|---|
| Pulse duration: | less than 100 ps | | |
| Number of pulses: | 100 | | |
| Camera filter: | 400 nm | | |
| Temperature: | 25° C. | | |

| Substance | τ(nS) solvent: (100 mM triethylammonium acetate) | (6M urea) | (6% acrylamide gel*) |
|---|---|---|---|
| D | 5 | 5 | — |
| AD | 5.3 | 5.0 | 4.4 |
| CD | 4.4 | 4.3 | 3.8 |
| TD | 2.1 | 2.7 | 2.8 |
| GD | 1.4 | 2.0 | 2.1 |

*(For preparation, see Sambrook, Fritsch, Maniatis; Molecular cloning 2; Cold Spring Harbor Laboratory Press 2nd edition 1989; section 13.47)

3. Identification of the Bases in a Thiodinucleotide by Means of Fluorescence Lifetimes The dye-labeling of the dinucleotides was carried out in the same way as that of the thionucleotides in Example 1, altering the reaction time (12 hours) and the reaction temperature (37° C.).

Dinucleotides (DNA strand numbered as usual in the 5'-3' direction) coupled to the dye (D) are called CAD, TAD, CCD, TCD and GCD. The fluorescence lifetimes were measured under the conditions described in Example 2. The fluorescence decay curve I(t) is described by the biexponential equation $$I(t)=(1-a_2)\exp(-t/\pi_1)+a_2\exp(-t/\pi_2)$$

The average fluorescence lifetime $\pi_{av}$ was calculated from:

$$\pi_{av} \approx (1-a_2)\pi_1 + a_2\pi_2$$

Fluorescence lifetimes π measured in 6M urea:

| Substance | $\tau_{av}$[ns] | $\tau_1$[ns] | $\tau_2$[ns] | $a_2$ |
|---|---|---|---|---|
| CAD | 3.8 | 4.5 | 0.9 | 0.20 |
| TAD | 3.1 | 3.8 | 0.7 | 0.23 |
| CCD | 3.7 | monoexponential | | |
| TCD | 2.9 | 3.8 | 0.8 | 0.29 |
| GCD | 2.5 | 3.6 | 0.6 | 0.37 |

4. DNA Sequencing with 2',3'-dideoxy-α-Thionucleotides and Specific Fluorescence Labeling

DESCRIPTION OF THE EXPERIMENTS

The single-stranded DNA to be sequenced is hybridized with an oligonucleotide (primer) which is complementary to the initial part of the sequence to be read. The hybrid forms the starting point of the DNA polymerase step (b).

The template-controlled polymerization entails synthesis, starting from the oligomer (primer) which is hybridized on, of a strand which is complementary to the DNA template which is to be sequenced. In each of 4 different reaction mixtures, a thiodeoxy analog mixed with the natural nucleotides was provided as terminator, thus achieving randomly distributed stops of the polymerase reaction on the growing opposite chain.

The DNA fragments with base-specific ends formed during the sequencing can be labeled either by conventional radioactive labeling techniques, for example by use of primer oligonucleotides labeled with $^{32}$P at the 5'end or by coupling fluorescence labels onto the thio functionality of the thio-2',3'-dideoxynucleotides after the enzymatic sequencing reaction has taken place.

Experimental Procedure

The sequence of the DNA fragment obtained when the HIV I pol reading frame is cut with the restriction enzymes Bgl I and Sal I is determined. The fragment to be sequenced is cloned in the vector M 13 mp 19 with BamH I and Sal I cleavage sites.

a. Hybridization of the DNA Template with a Kinase-Treated Primer Oligomer

The following were pipetted into an Eppendorf tube

2 µl of DNA solution, 100–300 µg/ml 0.5 µl of oligomer, 5 µg/ml (5'-GTAAAACGACGGCCA-3')

1 µl of buffer:
200 mM tris/HCl, pH 7.5, 100 mM $MgCl_2$,
10 mM dithioerythritol, 500 mM NaCl 6.5 µl of water and the reaction mixture was incubated at 65° C. for 60 min.

b. Sequencing Reaction with DNA Polymerase (Klenow Fragment)

The reaction mixture from a. was cooled to room temperature. Then 0.8 µl (=4 units) of DNA polymerase (Klenow fragment) was added, and the polymerization mixture was divided into four 2.5 µl portions on a microtiter plate.

3 µl of the particular sequencing mix were added to each to start the polymerization reaction.

The following 4 nucleotide solutions (the numbers indicate µmol/l)=sequencing mixes were used:

| µM | dTTP | dCTP | dGTP | dATP | particular thiodideoxynucleotide triphosphate in the mix |
|---|---|---|---|---|---|
| T Mix | 20 | 150 | 150 | 150 | 170 |
| C Mix | 150 | 10 | 150 | 150 | 150 |
| G Mix | 150 | 150 | 10 | 150 | 150 |
| A Mix | 150 | 150 | 150 | 10 | 170 |

The 4 mixtures were left to stand at room temperature for 20 min for the polymerization.

c. Fractionation and Detection

Fractionation and detection can be carried out by the 1-lane/1-dye principle described above or else by the 4-lane principle with radioactively labeled nucleotides.

The DNA strands were fractionated by electrophoresis by the method of Sanger and Coulson (FEBS Letters 87 (1978) 107) on 6% acrylamide/8M urea gels at 75 watts in 2 h. Autoradiographic detection revealed the same sequence as found by Ratner et al. (Nature 313 (1985) 277).

5. Nick Translation and in situ Hybridization with Fluorescence Detection by dye Coupling to Thionucleotides Description of the Experiments A nick translation is carried out to incorporate the thionucleotides into the probe DNA. The DNA probe (pUC 177) which binds specifically to the centromer region of human chromosome 1 was used. The in situ hybridization is carried out with a cell nucleus metaphase plate by the metaphase nuclei and the probe DNA being denatured together and subsequently renatured, it being possible for only the small probe DNA to hybridize onto chromosome 1. The hybridization which has taken place is observed under the fluorescence microscope.

Experimental Procedure
a. Nick Translation
Mixture:
1 µg of probe DNA (pUC177), V=2.5 µl , c=435 µg/ml
Thio-d-UTP: 10 µl, c=0.5 mM
dATP/dGTP/dCTP: 5 µl each, c=0.2 nM
Nick translation buffer: 5 µl
$H_2O$: 12.5 µl After the reaction solution had been mixed, 5 µl of enzyme solution were pipetted in and the mixture was incubated at 15° C. for 90 min. After the incubation time, the mixture was rapidly cooled on ice and the reaction was stopped by adding 50 µl of stop mix.

Solutions used:
Nick translation buffer:
Tris/HCl(pH: 7.2): 0.5 M
$MgSO_4$: 0.1 M
Dithiothreitol: $1 \times 10^{-3}$ mol/l
Bovine serum albumin (fraction V): 500 µg/ml
Enzyme solution:
DNA polymerase (E. coli): 0.4 U/ml
DNAase I (bovine pancreas): 40 pg/pl
Stop mix:
Bromophenol blue: 0.1%
Dextran blue: 0.5%
NaCl: 0.1 M
EDTA: 0.2 mM
Tris/HCl (pH 7.8): 0.2 mM b. In situ hybridization
Probe DNA mixture from step a)
Probe DNA (pUC 177): 10 µl
Formamide: 30 µl
20×SSC (pH 7):5 µl
$H_2O$: 5 µl
Solution used:
20×SSC (pH 7.0): NaCl 1.5 M
$Na_3$ citrate 0.15 M
Denaturation
Simultaneous denaturation of the probe DNA and the nuclei and metaphases fixed on the slide at 70° C. for 10 min.
Hybridization
At 40–42° C. overnight
Detection reaction and inspection
The slides were washed and then treated with dye-labeling solution:
Tris/HCl (1M) pH=7.8:5 µl $H_2O$/DMF (1:1): 45 µl
4,7-IEME-COUM: 0.5 µg The dye-labeling solution was then washed off, and the metaphases of the cell nuclei on the slide were inspected under the fluorescence microscope.

We claim:

1. A method for the enzymatic sequencing of DNA comprising (a) performing a template-controlled polymerization of deoxynucleotide triphosphates with a polymerase and a dideoxythio-nucleotide or a dideoxyamino-nucleotide as a terminator, to form a mixture of DNA fragments wherein each DNA fragment has a terminator bonded to one of its terminal bases which terminator;

(b) reacting the mixture of DNA fragments with one or two fluorescent dyes to couple at least one of the dyes to the terminator of each DNA fragment of the mixture;

(c) separating the dye labeled DNA fragments in one lane of a separation system, and (d) identifying the terminal bases of the DNA fragments to which the terminator has been coupled by measurement of the fluorescent lifetime of the fluorescent dye.

2. A method as claimed in claim 1, wherein fluorescent dyes are used as detector molecules.

3. The method of claim 1, wherein the separation is carried out by capillary electrophoresis, HPLC or electrophoresis.

4. The method of claim 1, wherein the characteristic influence on the fluorescent lifetime of the fluorescent dye bonded to the terminator is caused by photo-induced electron transfer between the DNA bases and the coupled dye.

5. The method of claim 1, wherein the terminator is coupled to the fluorescent dye prior to the polymerization.

* * * * *

UNITED STATES PATENT AND TRADEMARK OFFICE
CERTIFICATE OF CORRECTION

PATENT NO.   : 6,087,101
DATED        : July 11, 2000
INVENTOR(S)  : Greulich et al.

It is certified that error appears in the above-identified patent and that said Letters Patent is hereby corrected as shown below:

Column 9,
Line 10, claim 2 is printed incorrectly in total and should read:
-- 2. The method of claim 1, wherein the mixture of DNA fragments is reacted with two fluorescent dyes. --

Signed and Sealed this

Twelfth Day of November, 2002

*Attest:*

*Attesting Officer*

JAMES E. ROGAN
*Director of the United States Patent and Trademark Office*